United States Patent
Dickhans

(10) Patent No.: US 11,071,586 B2
(45) Date of Patent: Jul. 27, 2021

(54) COOLING SYSTEMS FOR ENERGY DELIVERY DEVICES

(71) Applicant: Covidien LP, Mansfield, MA (US)

(72) Inventor: William J. Dickhans, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 416 days.

(21) Appl. No.: 15/989,006

(22) Filed: May 24, 2018

(65) Prior Publication Data

US 2018/0344399 A1 Dec. 6, 2018

Related U.S. Application Data

(60) Provisional application No. 62/515,224, filed on Jun. 5, 2017.

(51) Int. Cl.
*A61B 18/14* (2006.01)
*A61B 18/18* (2006.01)
(Continued)

(52) U.S. Cl.
CPC .......... *A61B 18/1815* (2013.01); *A61B 18/14* (2013.01); *A61B 18/1492* (2013.01);
(Continued)

(58) Field of Classification Search
CPC . A61B 18/1815; A61B 18/14; A61B 18/1492; A61B 2018/00678; A61B 2018/00035; A61B 18/1477; A61B 2018/00821; A61B 2018/00809; A61B 2018/00708; A61B 2018/00642; A61B 2018/00863; A61B 2018/00672;
(Continued)

(56) References Cited

U.S. PATENT DOCUMENTS

| 3,739,777 A | 6/1973 | Gregg |
| 3,832,998 A | 9/1974 | Gregg |

(Continued)

FOREIGN PATENT DOCUMENTS

| CN | 104042338 A | 9/2014 |
| CN | 203915069 U | 11/2014 |

(Continued)

OTHER PUBLICATIONS

European Search Report dated Nov. 26, 2018, corresponding to counterpart European Application No. 18175785; 7 pages.

(Continued)

*Primary Examiner* — Linda C Dvorak
*Assistant Examiner* — Nils A Potter
(74) *Attorney, Agent, or Firm* — Carter, DeLuca & Farrell LLP

(57) ABSTRACT

A reservoir for supplying a cooling fluid to a medical ablation probe includes a wall defining a chamber therein, an outlet fluid port and an inlet fluid port each in fluid communication with the chamber, cooling fluid disposed within the chamber, and a thermochromic material thermally coupled to the cooling fluid. The thermochromic material is configured to exhibit a first color when the cooling fluid is below a threshold temperature, and a second color when the cooling fluid is above the threshold temperature.

9 Claims, 10 Drawing Sheets

(51) Int. Cl.
*A61B 18/00* (2006.01)
*A61B 18/12* (2006.01)

(52) U.S. Cl.
CPC ....... *A61B 18/1206* (2013.01); *A61B 18/1477* (2013.01); *A61B 2018/00023* (2013.01); *A61B 2018/00035* (2013.01); *A61B 2018/00083* (2013.01); *A61B 2018/00577* (2013.01); *A61B 2018/00642* (2013.01); *A61B 2018/00672* (2013.01); *A61B 2018/00678* (2013.01); *A61B 2018/00708* (2013.01); *A61B 2018/00809* (2013.01); *A61B 2018/00821* (2013.01); *A61B 2018/00863* (2013.01); *A61B 2018/1425* (2013.01); *A61B 2018/1823* (2013.01); *A61B 2018/1861* (2013.01); *A61B 2018/1869* (2013.01)

(58) Field of Classification Search
CPC .. A61B 2018/00577; A61B 2018/1869; A61B 18/1206; A61B 2018/00023; A61B 2018/1861; A61B 2018/00083; A61B 2018/1823; A61B 2018/1425; A61B 18/12; A61B 2018/00011; F25D 1/02
USPC .......................................................... 606/33
See application file for complete search history.

(56) References Cited

U.S. PATENT DOCUMENTS

| | | | |
|---|---|---|---|
| 3,990,443 | A | 11/1976 | Fletcher |
| 4,105,028 | A | 8/1978 | Sadlier et al. |
| 5,049,129 | A | 9/1991 | Zdeb et al. |
| 5,304,130 | A | 4/1994 | Button et al. |
| 5,411,052 | A | 5/1995 | Murray |
| 5,545,161 | A | 8/1996 | Imran |
| 5,733,319 | A | 3/1998 | Neilson et al. |
| 5,941,848 | A | 8/1999 | Nishimoto et al. |
| 6,036,680 | A | 3/2000 | Horne et al. |
| 6,478,793 | B1 | 11/2002 | Cosman et al. |
| 6,506,189 | B1 | 1/2003 | Rittman, III et al. |
| 6,514,251 | B1 | 2/2003 | Ni et al. |
| 6,575,969 | B1 | 6/2003 | Rittman, III et al. |
| 6,679,865 | B2 | 1/2004 | Shekalim |
| 6,979,120 | B1* | 12/2005 | Wolfe ...................... G01K 3/04 116/216 |
| 7,052,463 | B2 | 5/2006 | Peszynski et al. |
| 7,425,208 | B1 | 9/2008 | Vitello |
| 8,038,670 | B2* | 10/2011 | McClurken ........ A61B 18/1482 606/41 |
| 8,292,880 | B2 | 10/2012 | Prakash et al. |
| 8,308,726 | B2 | 11/2012 | Kumar et al. |
| 8,334,812 | B2 | 12/2012 | Brannan |
| 8,430,871 | B2 | 4/2013 | Brannan |
| 9,101,344 | B2 | 8/2015 | Larson et al. |
| 9,962,214 | B2 | 5/2018 | Larson et al. |
| 2004/0127840 | A1 | 7/2004 | Gara et al. |
| 2004/0267339 | A1 | 12/2004 | Yon et al. |
| 2006/0031099 | A1 | 2/2006 | Vitello et al. |
| 2006/0272120 | A1* | 12/2006 | Barrick ................... G01F 23/58 15/321 |
| 2007/0060915 | A1 | 3/2007 | Kucklick |
| 2008/0051732 | A1 | 2/2008 | Chen |
| 2009/0145349 | A1 | 6/2009 | Hebert |
| 2009/0149930 | A1 | 6/2009 | Schenck |
| 2009/0222002 | A1 | 9/2009 | Bonn et al. |
| 2010/0053015 | A1 | 3/2010 | Willyard |
| 2010/0057074 | A1 | 3/2010 | Roman et al. |
| 2010/0228162 | A1 | 9/2010 | Sliwa et al. |
| 2011/0077637 | A1* | 3/2011 | Brannan ................. A61B 90/06 606/33 |
| 2011/0118724 | A1 | 5/2011 | Turner et al. |
| 2011/0230753 | A1* | 9/2011 | Mahon .................. A61N 7/022 600/411 |
| 2011/0295245 | A1 | 12/2011 | Willyard et al. |
| 2012/0039355 | A1* | 2/2012 | Wolosuk ................ G01K 11/12 374/155 |
| 2012/0323296 | A1 | 12/2012 | Takeda et al. |
| 2013/0030426 | A1 | 1/2013 | Gallardo et al. |
| 2013/0178841 | A1 | 7/2013 | Reid, Jr. |
| 2013/0237901 | A1 | 9/2013 | Woo |
| 2014/0081218 | A1 | 3/2014 | Winawer et al. |
| 2014/0209486 | A1 | 7/2014 | Chen |
| 2014/0262201 | A1 | 9/2014 | Larson et al. |
| 2014/0276033 | A1 | 9/2014 | Brannan et al. |
| 2014/0276740 | A1* | 9/2014 | Larson .................... F16L 39/00 606/33 |
| 2014/0281961 | A1 | 9/2014 | Baker |
| 2014/0350401 | A1* | 11/2014 | Sinelnikov ......... A61B 17/2202 600/439 |
| 2016/0022477 | A1* | 1/2016 | Schaefer .................. A61F 7/00 607/104 |

FOREIGN PATENT DOCUMENTS

| | | |
|---|---|---|
| CN | 209392085 U | 9/2019 |
| EP | 2540260 A1 | 1/2013 |
| EP | 2550924 A1 | 1/2013 |
| EP | 2777765 A2 | 9/2014 |
| JP | S55159393 A | 12/1980 |
| JP | 2004097402 A | 4/2004 |
| KR | 101016566 B1 | 2/2011 |
| WO | 2004034940 A1 | 4/2004 |
| WO | 2011056684 A2 | 5/2011 |
| WO | 2011063061 A2 | 5/2011 |

OTHER PUBLICATIONS

Partial European Search Report dated Jun. 3, 2014 issued in European Application No. 14159833.4; 6 pages.
European Search Report, dated Oct. 1, 2014, issued in European Application No. 14 15 9833.4; 12 pages.
Chinese Office Action (with English translation), dated Oct. 17, 2016, issued in Chinese Application No. 201410093847.9; 16 total pages.
Chinese Office Action (English translation), dated Apr. 15, 2016, issued in Chinese Application No. 201410093847.9; 10 pages.
Japanese Office Action (with English translation), dated Jan. 16, 2018, issued in Japanese Application No. 2014-045881; 10 pages.
Australian Office Action, dated Mar. 1, 2018, issued in Australian Application No. 2014201315; 4 pages.
Chinese Office Action dated Oct. 30, 2020, issued in corresponding Chinese Appln. No. 201810570309.

* cited by examiner

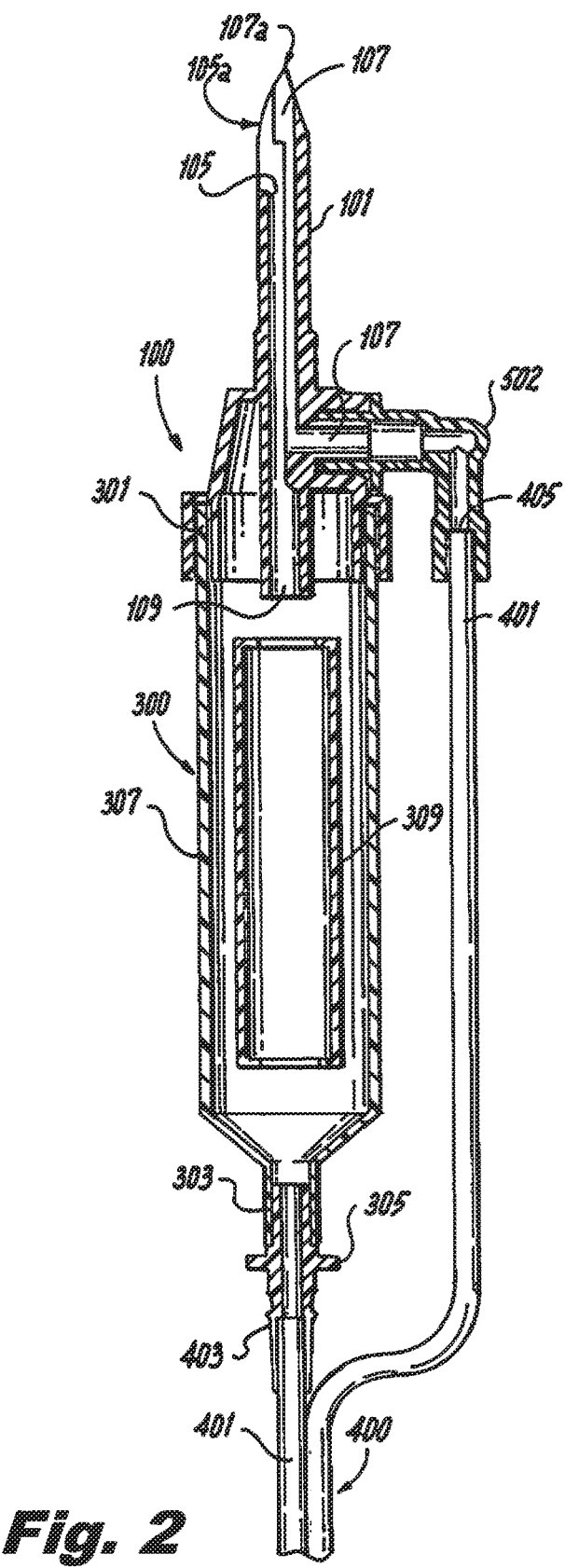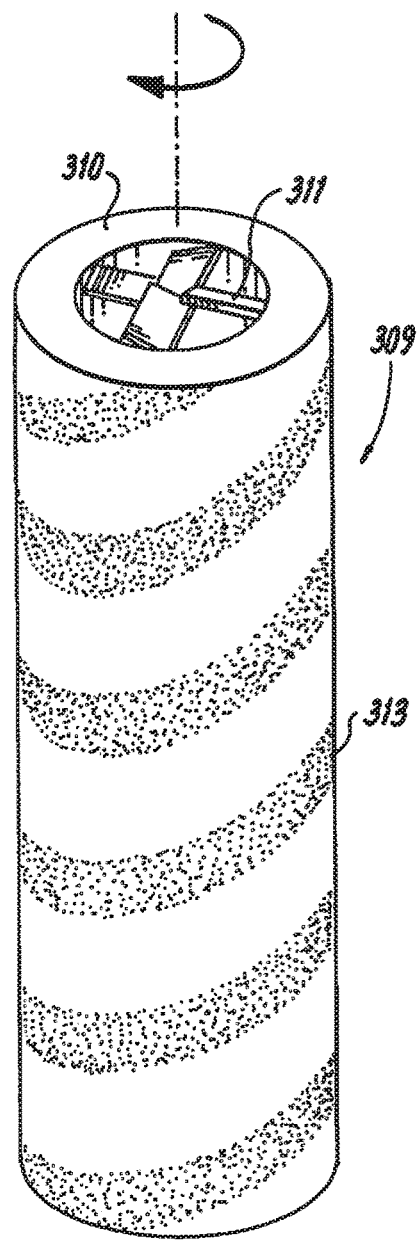
Fig. 2
Fig. 3

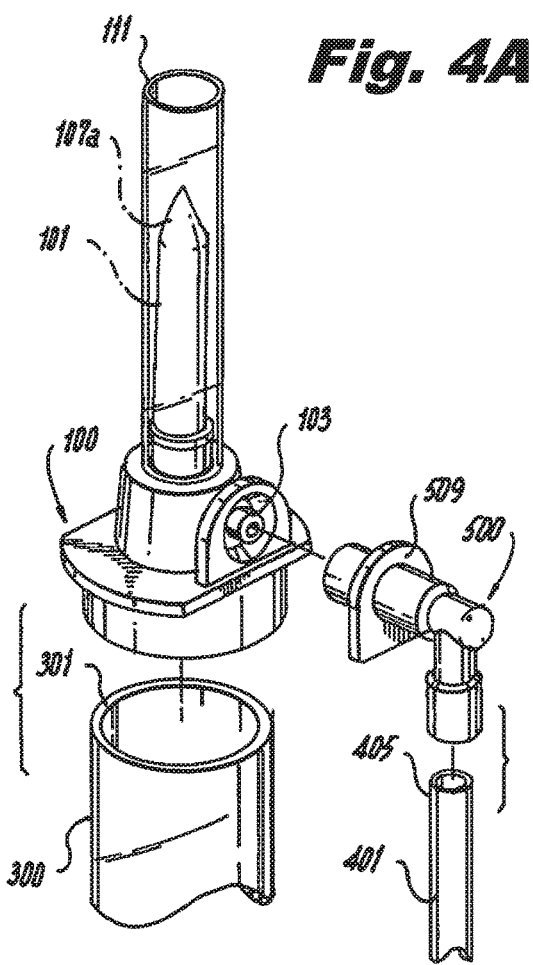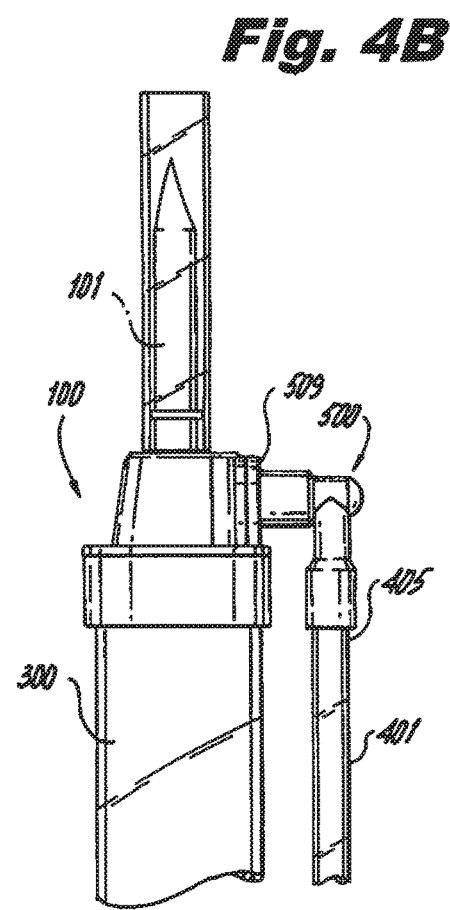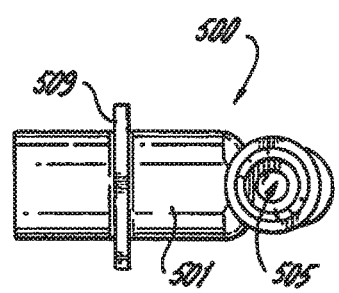
Fig. 4A  Fig. 4B
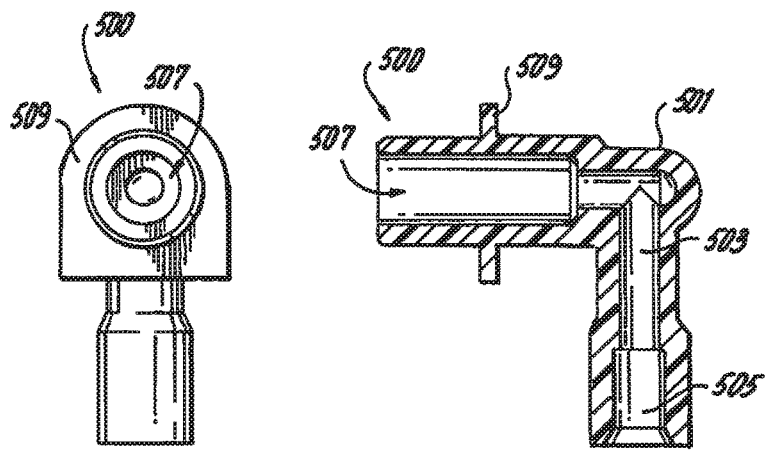
Fig. 5A  Fig. 5B  Fig. 5C

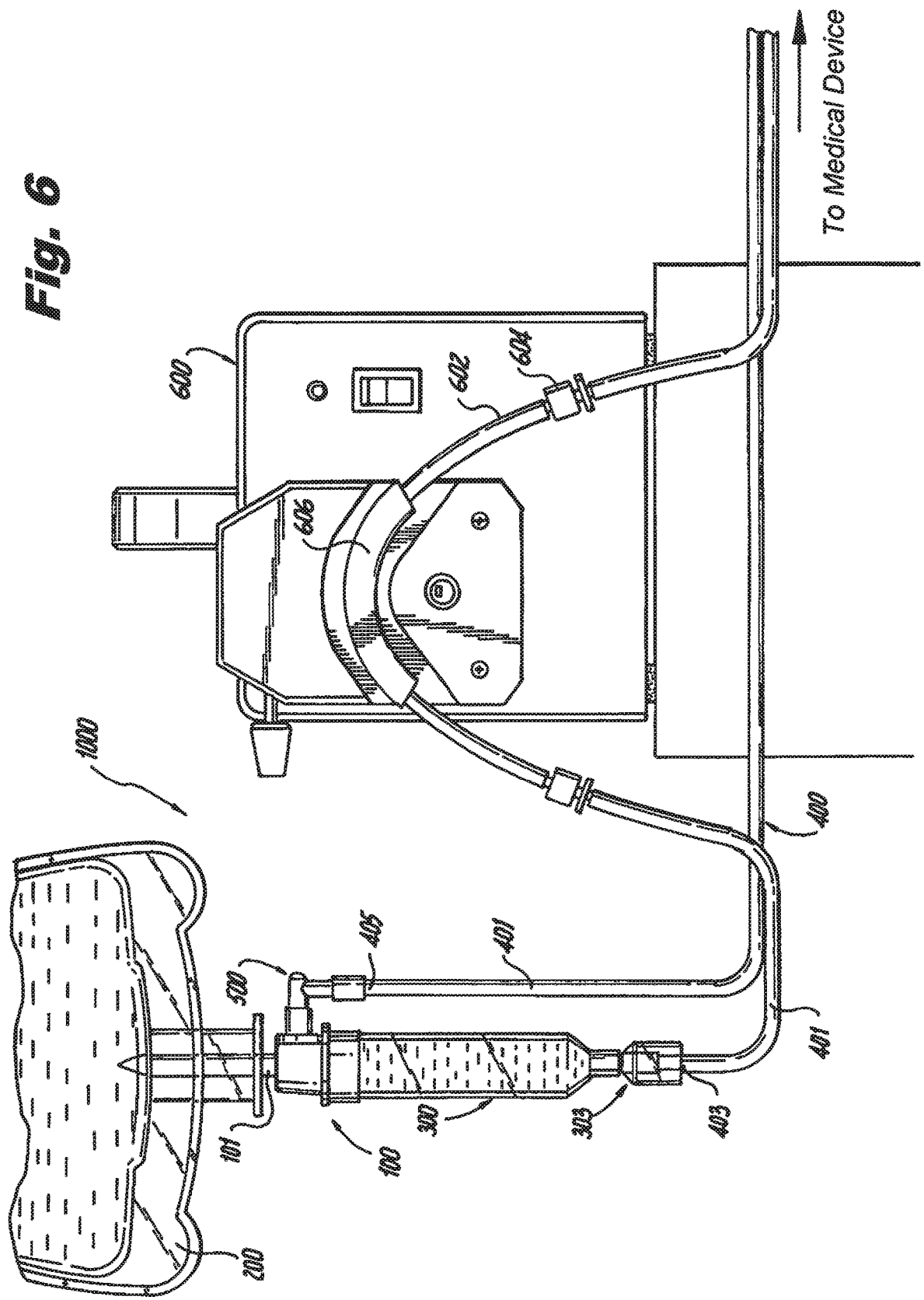

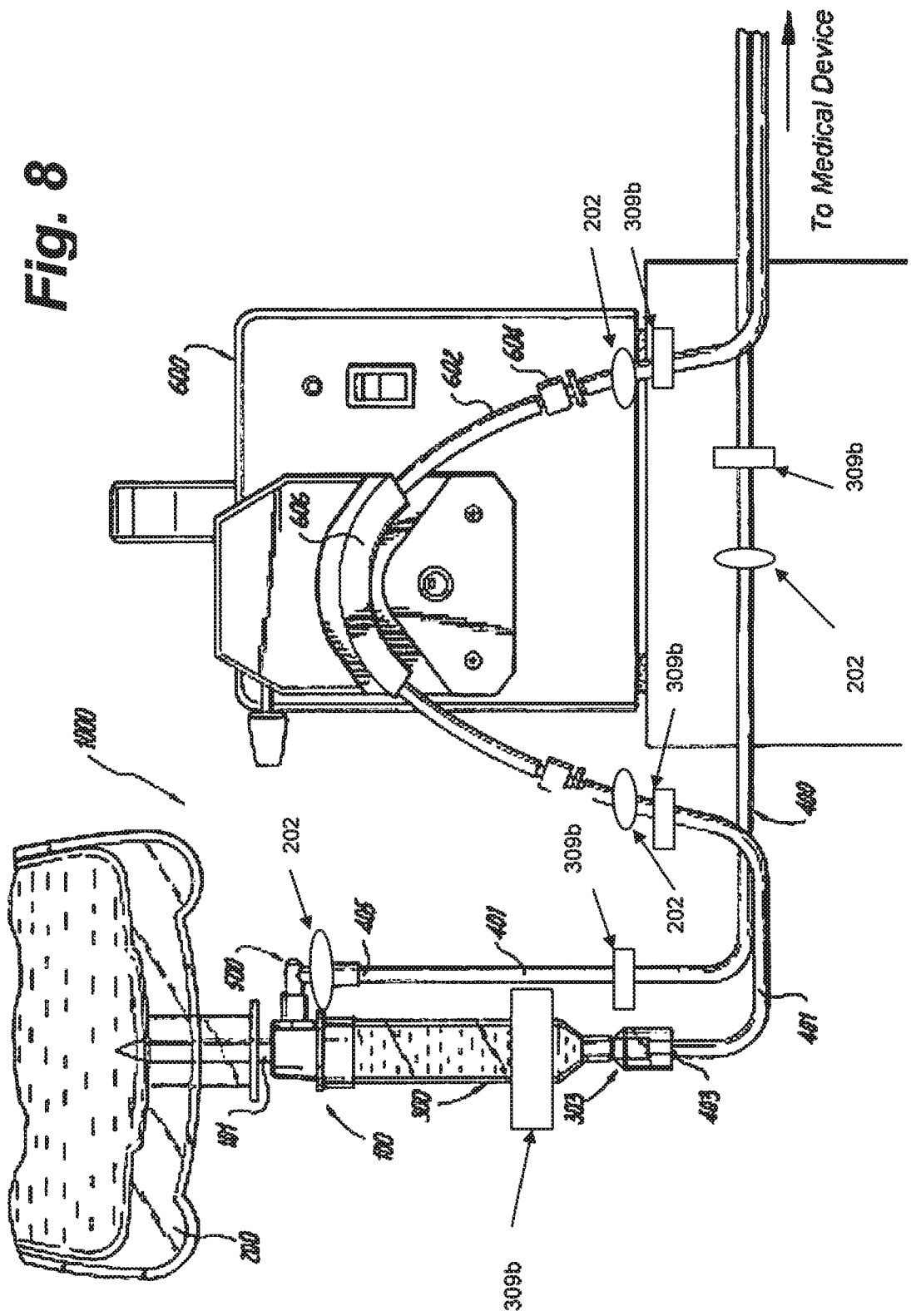

COOLING SYSTEMS FOR ENERGY DELIVERY DEVICES

BACKGROUND

1. Technical Field

The present disclosure relates to the use of energy delivery devices. More particularly, the present disclosure is directed to cooling systems for energy delivery devices.

2. Background of the Related Art

Energy delivery procedures such as tissue ablation are used in numerous medical procedures to treat many conditions. Ablation can be performed to remove undesired tissue such as cancer cells. Ablation procedures may also involve the modification of the tissue without removal, such as to stop electrical propagation through the tissue in patients with an arrhythmia condition. Often the ablation is performed by passing energy, such as electrical energy, through one or more electrodes and causing the tissue in contact with the electrodes to heat up to an ablative temperature.

Electromagnetic (EM) ablation may also be used instead of direct energy discharge into tissue. For example, microwave (MW) ablation is a common example of such EM ablation where energy is applied to tissue through microwave radiation. EM ablation devices may require cooling to operate within desired parameters without damaging the ablation device or causing unintended tissue damage. Examples of EM ablation medical devices include percutaneous needle ablation probes and flexible intraluminal ablation catheters. Some devices implement cooling systems including a peristaltic pump that forces saline or another fluid through a tubing system operably connected to an energy delivery device. The saline solution draws heat from the energy delivery device and is then pumped out into a receptacle or to a drain. However, these systems require constant supply of saline bags, can be wasteful, and can be inefficient. In addition, it is often difficult for a clinician to determine whether the saline solution has warmed to a temperature that is no longer suitable for cooling the energy delivery device.

SUMMARY

Accordingly, the present disclosure provides a medical ablation device cooling system including an outlet tube configured to be coupled to an outlet fluid port of an ablation probe and an inlet tube configured to be coupled to an inlet fluid port of the ablation probe. The cooling system further includes a reservoir containing a cooling fluid and a thermochromic material thermally coupled to the cooling fluid. The reservoir is configured to be coupled to the ablation probe via the outlet and inlet tubes. The thermochromic material is configured to exhibit a first color when the cooling fluid is below a threshold temperature, and a second color when the cooling fluid is above the threshold temperature.

In embodiments, the thermochromic material may be disposed within the reservoir and/or outside of the reservoir.

In embodiments, the cooling system may further include a float disposed within the reservoir for indicating the level of the cooling fluid within the reservoir. The thermochromic material may be coupled to the float.

In embodiments, the thermochromic material may be coupled to a wall of the reservoir.

In embodiments, the cooling system may include a sticker adhered to the wall of the reservoir, and the thermochromic material may be coupled to the sticker.

In embodiments, the first color may be associated with a cool temperature, and the second color may be associated with a warm temperature.

In embodiments, the threshold temperature may be between approximately 10° C. and approximately 60° C.

In embodiments, the cooling system may further include a drip chamber fluidly coupling the reservoir and the outlet tube. The thermochromic material may be coupled to the drip chamber.

In embodiments, the reservoir may be a saline bag.

In another aspect of the present disclosure, a reservoir for supplying a cooling fluid to a medical ablation probe is provided. The reservoir includes a wall defining a chamber therein, an outlet fluid port and an inlet fluid port each in fluid communication with the chamber, cooling fluid disposed within the chamber, and a thermochromic material thermally coupled to the cooling fluid. The thermochromic material is configured to exhibit a first color when the cooling fluid is below a threshold temperature, and a second color when the cooling fluid is above the threshold temperature.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2 is a cross-sectional view of a drip chamber and flow indicator, in accordance with the present disclosure;

FIG. 3 is a perspective view of a flow indicator of a cooling system in accordance with the present disclosure;

FIG. 4A is an exploded view of a portion of the cooling system in accordance with the present disclosure;

FIG. 4B is a side view of the portion of the cooling system of FIG. 4A;

FIG. 5A is a cross-sectional view of a fluid return elbow member in accordance with the present disclosure;

FIG. 5B is a front view of the fluid return elbow of FIG. 5A;

FIG. 5C is a bottom view of the fluid return elbow of FIG. 5A;

FIG. 6 is a side view of a cooling system in accordance with the present disclosure;

FIG. 8 is a side view of a cooling system in accordance with the present disclosure depicting locations of flow sensors and thermocouples;

DETAILED DESCRIPTION

Figure 1:
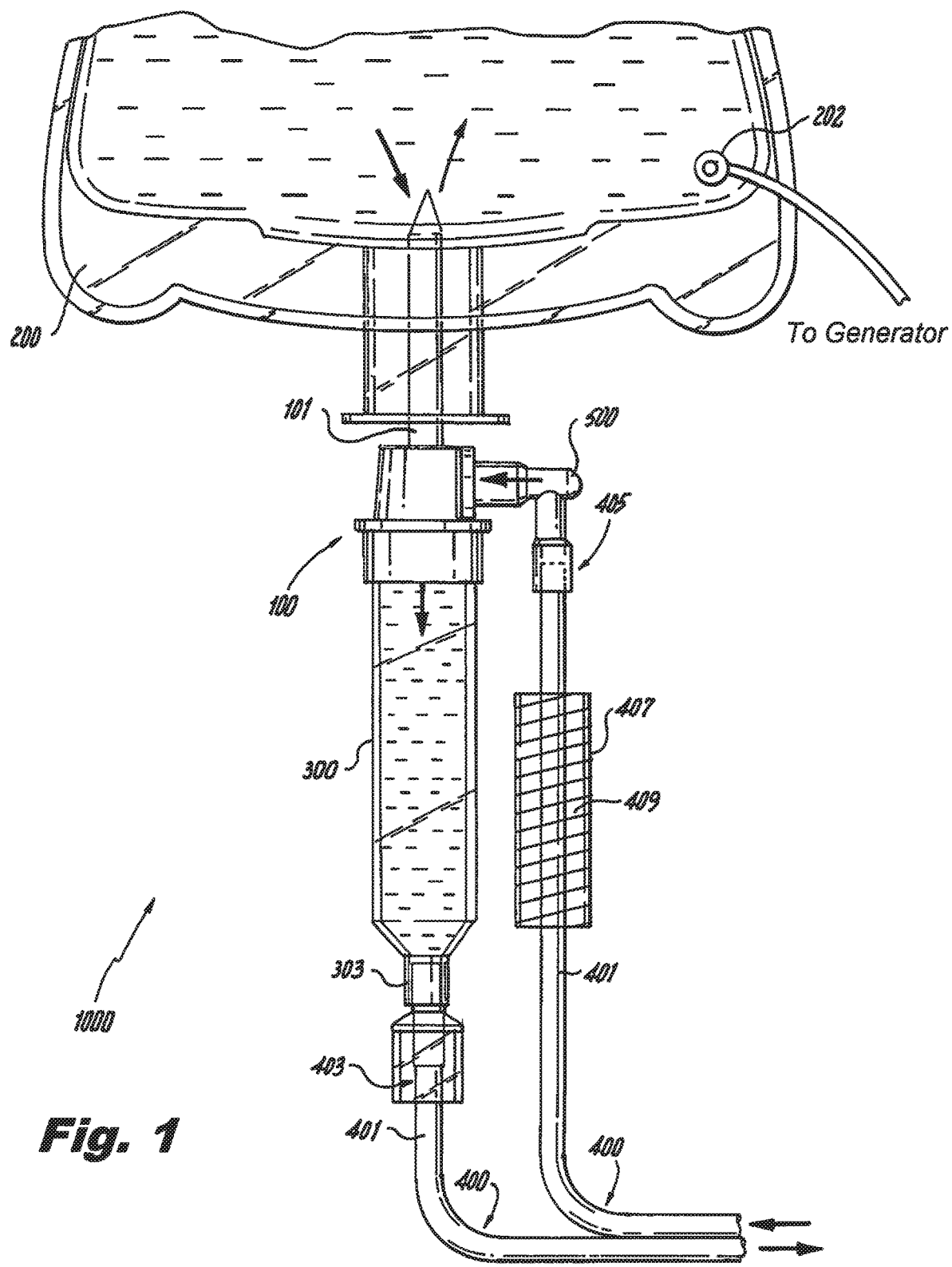
FIG. 1 is a side view of a portion of a cooling system in accordance with the present disclosure.

Particular embodiments of the present disclosure are described hereinbelow with reference to the accompanying drawings; however, the disclosed embodiments are merely examples of the disclosure and may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as, for example, microwave ablation or radiofrequency (RF) ablation. As it is used in this description, "fluid" generally refers to a liquid, a gas, or both.

In accordance with at least one aspect of the present disclosure, an energy delivery device cooling system is disclosed. Referring generally to FIGS. 1-6, the system 1000 includes a reservoir connector assembly 100 in communication with a reservoir 200. The reservoir 200 is configured to contain or hold a cooling fluid. The reservoir connector assembly 100 may include an elongate member 101 configured to extend into the reservoir 200. Tubing system 400 connects the reservoir 200 with a medical device having inlet and outlet ports and forming a closed loop cooling system 1000, as will be described in greater detail below.

In some embodiments, the elongate member 101 can have any length and shape capable of being inserted into the reservoir 200. For example, the elongate member 101 can be a spike with a penetrating tip. In other embodiments, the elongate member 101 can have a blunt or substantially flat tip. The elongate member 101 can be substantially cylindrical, and in the embodiments with a piercing tip, the tip can be symmetrically conical or non-symmetrically conical.

Referring specifically to FIG. 2, the elongate member 101 has at least a first lumen 105 and a second lumen 107 defined therethrough. Each lumen 105, 107 is configured to be in fluid communication with the reservoir 200 shown in FIG. 1 at openings 105a and 107a respectively. The first lumen 105 may act as an inflow lumen for drawing fluid from the reservoir 200 and the second lumen 107 may act as a return lumen for returning fluid to the reservoir 200.

Lumens 105, 107 and openings 105a, 107a may have the same or different diameters. The diameter of the lumens 105, 107 may be selected based on a desired volumetric flow rate and fluid velocity for a given medical device. For example, to promote mixing in the reservoir 200, a smaller diameter lumen 107 can be chosen to achieve a higher velocity of the fluid for a given pressure. The increased velocity can increase turbulent flow within the reservoir 200 and/or the tubing system 400, resulting in increased mixing of the fluid. This increased mixing can promote homogenization of the fluid temperature within the reservoir 200 and/or the tubing system 400. The turbulent flow can also increase the efficiency of the transfer of heat from the fluid to the surrounding environment.

At least one outflow port 109 is in fluid communication with the first lumen 105 and allows fluid to flow from the reservoir 200 into a drip chamber or directly into the tubing system 400. With continued reference to FIG. 2 and added reference to FIG. 4A, the reservoir connector assembly 100 includes a return port 103 configured to allow cooling fluid to return to the reservoir connector assembly 100 from the tubing system 400. The return port 103 is in fluid communication with the second lumen 107 and may be configured to allow for direct or indirect fluid communication with tubing system 400. It is also envisioned that the reservoir connector assembly 100 includes more than one return port 103.

In some embodiments, the elongate member 101 further includes a third lumen and a fourth lumen having third and fourth openings, respectively, and in fluid communication with the reservoir 200 and the outflow port 109. Similarly, added lumens may also connect to the return port 103.

The elongate member 101 or the reservoir 200 may include a thermocouple 202 operably connected thereto to monitor a temperature of the fluid inside the reservoir 200. Alternatively, the thermocouple 202 may be placed in various locations to measure the temperature of the fluid in the system 1000, as shown in FIG. 8. For example, the thermocouple 202 may be placed near the opening of the second lumen 107 to measure the temperature of the fluid flowing into the reservoir 200, near the first lumen 105 to measure the temperature of the fluid flowing out of the reservoir 200, in a portion of the tubing system 400 to measure the temperature of fluid flowing therein, or any combination thereof. The thermocouple 202 may be connected to an energy source for the medical device, for example a microwave generator (not shown), and may be employed as a safety shut off for the energy source such that if the temperature of the fluid rises beyond a set threshold that indicates insufficient cooling, the energy source is shut off to prevent undesired damage to patient tissue during treatment.

As shown in FIG. 1, a reservoir connector assembly 100 fluidly connects the reservoir 200 with a drip chamber 300. The drip chamber 300 may include a top portion 301 (FIG. 4A) configured to receive a portion of the reservoir connector assembly 100 and a bottom portion 303 configured to connect the drip chamber 300 in fluid communication with the tubing system 400. In embodiments, a fluid connector 305 connects the bottom portion 303 with the tubing system 400 and facilitates fluid communication therebetween. Between the top portion 301 and the bottom portion 303 is a central portion 307, which may be formed as a cylinder. As shown in FIGS. 2, 7, and 8, the central portion 307 of the drip chamber 300 may also include a flow indicator 309 for indicating that a fluid is flowing from the reservoir 200 through the drip chamber 300 to the tubing system 400.

As shown in FIG. 3, the flow indicator 309 may be formed of a hollow cylinder 310 with hydrofoils 311 configured to rotate the hollow cylinder 310 in the drip chamber 300 when fluid flows through the flow indicator 309. The flow indicator 309 may include a design 313 disposed on an outer surface thereof that visually indicates that the cylinder 309 is rotating, and thus that fluid is flowing therethrough. For example, the design 313 may resemble a barber-shop pole, however, other designs can be used to indicate fluid flow, for example a corporate logo COVIDIEN® or other graphic design. The cylinder 310 may be formed of a material with a specific gravity causing the cylinder 310 to either be neutrally buoyant in the cooling fluid or to float in the cooling fluid. Other embodiments of flow indicators 309 may be utilized that are suitable for indicating flow in the drip chamber 300 including but not limited to low density balls, floating material indicators, paddle wheel indicators, or the like.

Figure 7A:
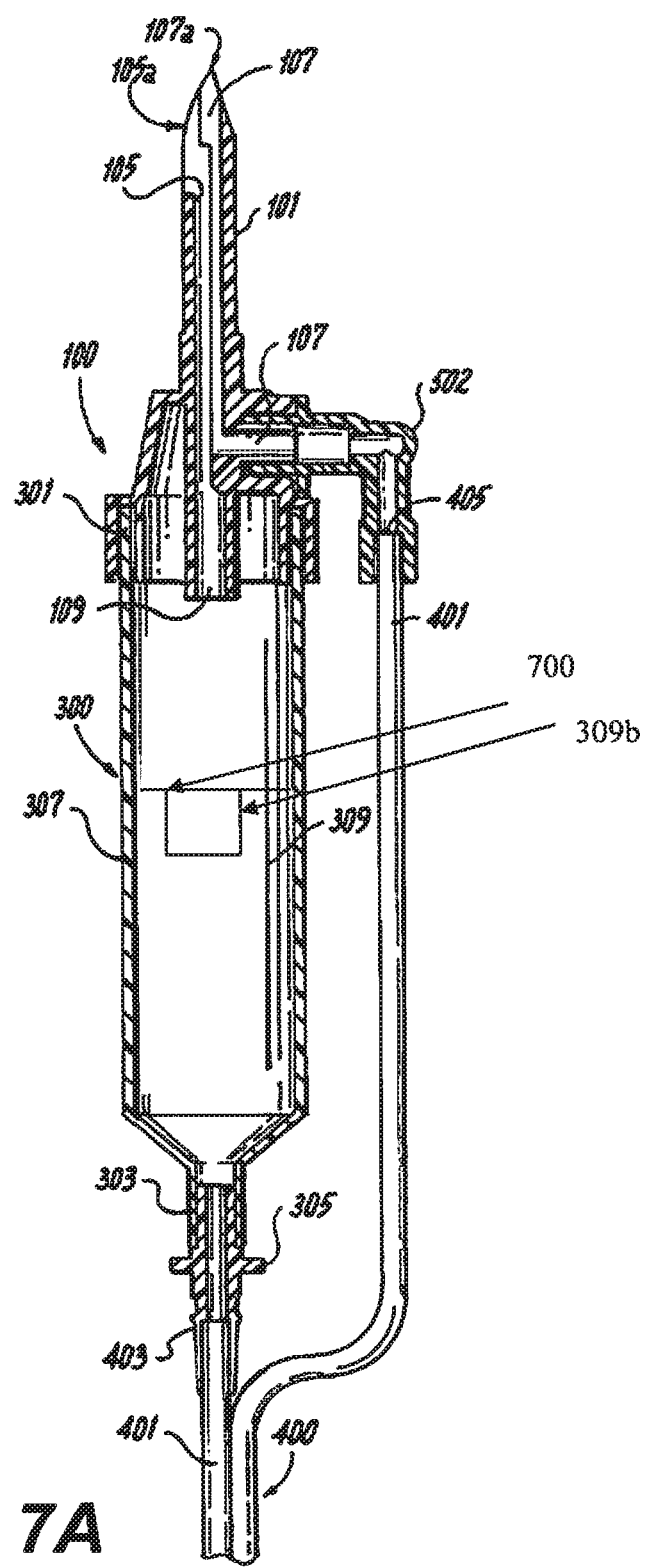
FIGS. 7A and 7B are cross-sectional views of a drip chamber and a flow indicator, in accordance with the present disclosure.
Figure 7B:
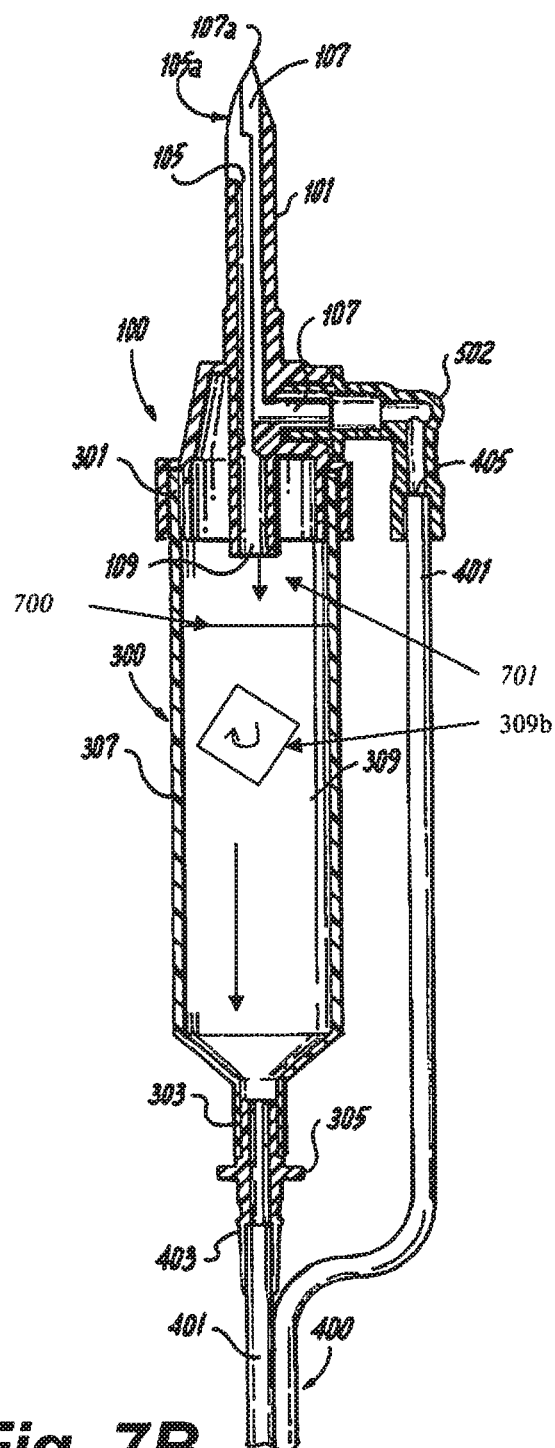

An alternative arrangement of a flow indicator 309a is depicted in FIGS. 7A and 7B. As shown in FIGS. 7A and 7B, the flow indicator 309a is generally in the shape of a cube, though other geometric shapes may be employed without departing from the scope of the present disclosure. The cube shape may be advantageous by eliminating the possibility of the flow indicator 309a occluding the bottom portion 303 of the drip chamber 300 when the system 1000 is initially primed with the fluid. The flow indicator 309a has a density related to the cooling fluid such that when fluid is not flowing through the drip container 300 the flow indicator 309a floats to the upper surface 700 of the fluid in the drip container 300 as shown in FIG. 7A and when fluid is flowing through the drip container 300 the flow indicator 309a partially submerges beneath the surface 700 and may also rotate to provide visual indicia of fluid flow as shown in FIG. 7B.

The tubing system 400 may include one or more return fluid flow indicators disposed thereon to indicate that a fluid is returning from the medical device to the reservoir 200 through tubing system 400. Examples of such return flow indicator include bubble indicators and traps, Venturi-style indicators, Hall-effect fluid flow indicators, and the like. Indicators, such as bubble indicators and venturi devices, also have the dual purpose of removing any gas which may have entered the system or vapor from the liquid flow to prevent disruption in the flow. Other fluid flow indicators may also be employed to measure fluid velocity, pressure, or volumetric flow rate. Examples of the fluid flow indicators are currently sold by Introtek International under the name BDC and BER Ultrasonic Clamp-on Air Bubble, Air-in-line & Liquid level Detection Systems as well as the Drip Chamber Ultrasonic Liquid Level Sensors.

FIG. 8 illustrates numerous locations where flow indicators 309b and thermocouples 202, as described above, may be employed within system 1000. The flow indicators 309b are flow sensors that detect flow of a fluid between portions of the flow indicators 309b. The flow indicators 309b and thermocouples 202 may be attached to various portions of the system 1000 and may be attached to devices (not shown) that provide audible and/or visual indicia of fluid flow within the system 1000. Further, the devices themselves may provide audible and/or visual indicia when fluid is not flowing within portions of the system 1000, e.g. when a tube is kinked or blocked.

Referring now to FIGS. 1 and 2, the tubing system 400 includes one or more tubes 401 that allow a fluid to flow from the reservoir connector assembly 100, through an energy delivery device 12 (see FIG. 9) such as an ablation needle or catheter or an energy source, and back to the reservoir connector assembly 100. The tubing system 400 may include a first end 403 and a second end 405.

In the illustrated embodiment, the first end 403 is in fluid communication with the outflow port 109, either indirectly through the bottom portion 303 of drip chamber 300 or by direct connection to outflow port 109, and is configured to allow fluid to flow into tubing system 400. The second end 405 is in fluid communication with the return port 103, and is configured to allow fluid to return to the reservoir 200 through the second lumen 107.

Tubing system 400 may also include one or more thermal diffusion devices 407 configured to draw heat from the fluid and diffuse the heat to the ambient environment. As shown in FIG. 1, the thermal diffusion device 407 includes a series of fins 409 in contact with the tube 401 returning from a medical device. A fan may be employed to direct airflow over the fins and increase the cooling effect. While shown connected to the tube 401, a thermal diffusion device 409 could also or alternatively be employed on the reservoir 200. A further alternative could employ passing the tube 401 returning from the medical device through a reservoir containing cold water or ice water in order to further draw heat out of the fluid flowing through the tubes 401.

The system 1000 may further include an elbow member 500 connected to the second end 405 of the tubing system 400 as shown in FIGS. 5A-C. The second end 405 of the tubing system 400 in fluid communication with the return port 103 through the elbow member 500.

The elbow member 500 may include a body 501 defining a lumen 503, an inflow port 505 in fluid communication with the lumen 503, and an outflow port 507 in fluid communication with the lumen 503. The inflow port 505 is configured to connect to a return section or second end 405 of a tubing system 400, and the outflow port 507 is configured to connect to or accept the return port 103 of the reservoir connection assembly 100.

The elbow member 500 may further have a flange 509 disposed around the outflow port 507 to ensure proper alignment of the elbow 500 with the reservoir connection assembly 100 as shown in FIGS. 4A and 4B. For example, as shown, flange 509 has a tombstone shape with a flat portion on a bottom portion thereof to allowing for connection with return port 103 in only one orientation of the elbow 500.

In at least some embodiments, the elbow 500 is formed of molded plastic. The elbow 500 may be injection molded, blow molded, or formed in any other suitable manner known in the art. The elbow 500 may be made of one solid piece or a conglomeration of subparts.

In one embodiment, one or more pumps may be used to control fluid flow through the cooling system 1000. Referring to FIG. 6, a pump 600 may be connected to the tubing system 400 to pressurize a fluid in the tubing 401. While any pump known in the art can be used, as shown FIG. 6, the type of pump 600 used is a peristaltic pump which applies pressure to compress the outside of a pump tubing 602 forcing fluid downstream towards the medical device. The pump tubing 602 may be made of a thicker gauge of the same material or a different material than the tubing 401, thus allowing it to withstand the repetitive stresses of the peristaltic pump for the duration of a medical procedure. Connectors 604 may be used to fluidly connect the pump tubing 602 to the tubing 401. Further, a protective slip cover 606 may alternatively be used to protect either the pump tubing 602, or the tubing 401, if no pump tubing 602 is utilized. Though described herein with respect to a peristaltic pump, any device suitable to create a pressure to advance fluid through the tubing 401 in the cooling system 1000 may be used.

As an alternative to using a peristaltic pump 600, the entire system 1000 may rely on gravity and the change in density of the fluid as it is heated to allow the fluid to circulate through the system 1000. For example, as water heats, its density at 1 atm (sea level) decreases from about 62.4 lb/ft$^3$ at 60° F. to about 60 lb/ft$^3$ at 212° F. This difference in density may in some circumstances promote sufficient circulation of the fluid through the system 1000 to maintain proper cooling of the medical device.

The fluid used in cooling system 1000 may be any suitable liquid such as saline solution, de-ionized water, sugar water, and combinations thereof, or the like. For example, the reservoir 200 may be a saline bag traditionally used in medicine.

In use, the tubing system 400 is connected to a medical device (not shown) to cool the medical device. The medical device may have cooling lumens such as those found in microwave ablation probes and microwave ablation catheters. The tubing system 400 connects to an inflow port of the medical device allowing cooling fluid to flow through the lumens of the medical device to and flow out of an outflow port on the medical device. The cooling fluid may pumped from the reservoir 200 through the medical device, as described above, or alternatively, the cooling fluid may be gravity fed to the medical device. The cooling system 1000 may include the reservoir connection assembly 100 and the drip chamber 300 in fluid communication with the tubing system 400, as described above. The cooling fluid flows from the reservoir 200 through the reservoir connection assembly 100, drip chamber 300, and the tubing system 400 into the inflow port of the medical device. The fluid returns to the reservoir 200 flowing from the outflow port of the medical device through tubing system 400, the return port 103, and the second lumen 107 of reservoir connection assembly 100. The fluid extracts or absorbs heat from the medical device to cool the device. As the fluid is traveling through system 1000, it releases some heat into the environment surrounding the tubing system 400. If thermal diffusion devices 407 are connected to the system 1000, heat may be released from the fluid more efficiently, allowing for a reduced operating temperature of the system 1000.

Temperatures maintained in the system 1000 and the energy delivery device should be within a range to avoid injury to the patient and adequate to allow flow through the system. For example, the temperature should be below approximately 113° F. to avoid injury to the patient and above the freezing temperature of the fluid. Pressures and flow rates within the system 1000 and the components thereof may be varied through variations in pump speed, and through design of the system 1000 and the components thereof.

One of the advantages of the cooling system 1000 described herein is that it can employ standard sterile saline bags as the fluid reservoir, which eliminates the need for a specialized fluid source. Further the system 1000 recirculates fluid as opposed to simply dumping the cooling fluid after one pass through the medical device, thereby conserving cooling fluid and eliminating the need for a collection bucket or bag.

Methods are also disclosed herein. In an embodiment, a method may include providing a saline bag or other fluid reservoir and a saline bag elongate member having multiple lumens defined therein. The saline bag elongate member includes at least one return port connected to at least one of the lumens. The method may also include providing a drip container such as the drip container 300 disclosed herein.

The method may further include providing an elbow 500 as disclosed herein. The method further includes connecting the elbow 500 to the return port of the saline bag elongate member to allow fluid flow to return into the saline bag through the return port. The method also includes the step of connecting a return portion of the tubing system 400 to the elbow 500.

Also disclosed is a method for recirculating a cooling fluid for use with an energy delivery device. The method includes providing an energy delivery device, providing a recirculating cooling system connected to the energy delivery device, and recirculating a fluid through the cooling system and energy delivery device to maintain the energy delivery device at a desired temperature or within a desired temperature range to prevent undesired damage to tissue. The desired temperature range may include an upper limit corresponding to a temperature above which tissue is damaged and a lower limit below which the fluid will not flow within the system. The flow rate of fluid within the system may be adjusted as the temperature approaches the upper limit or the lower limit. For example, when the temperature approaches the upper limit the flow rate may be increased to increase the cooling of the medical device. The system may include visual or audible indicia when the temperature approaches the upper or lower limit.

Figure 9:
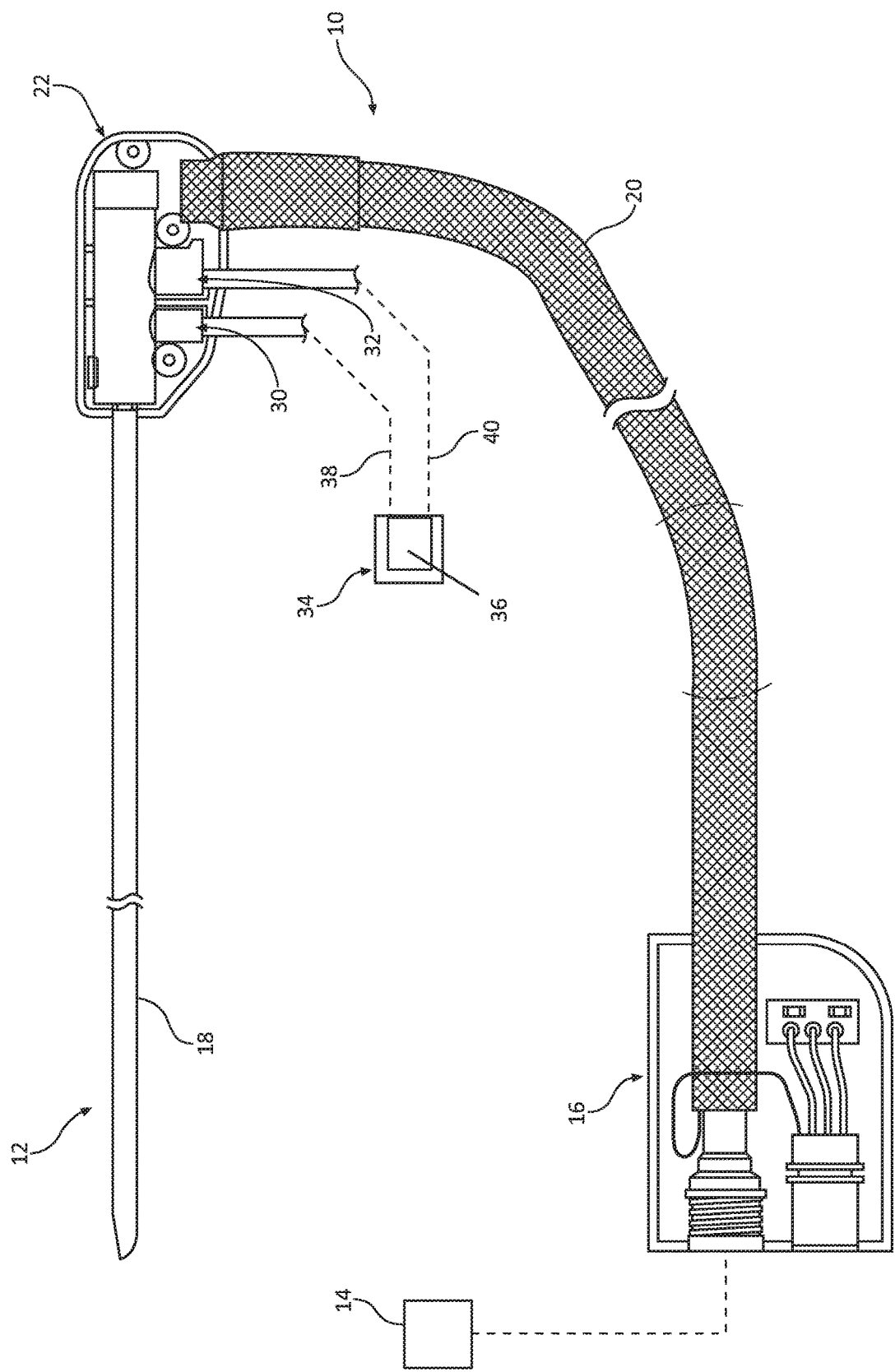
FIG. 9 is a schematic illustration of a microwave ablation system including a cooling system.
Figure 10:
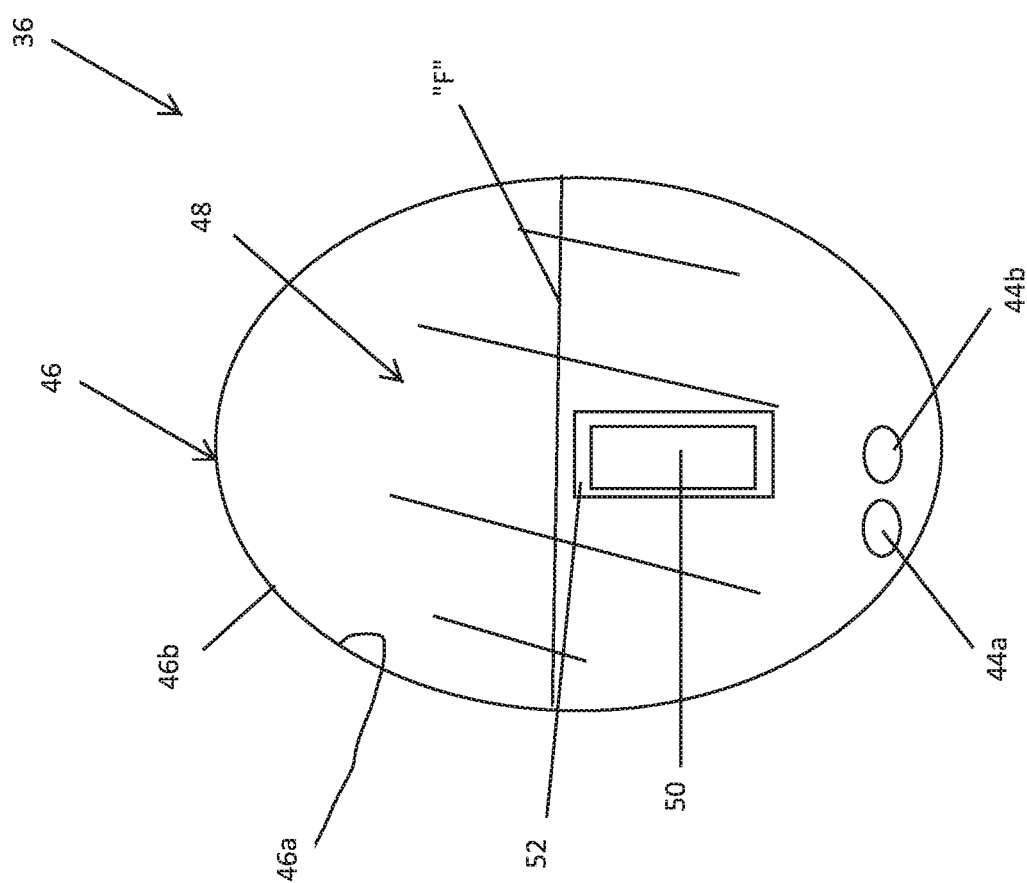
FIG. 10 is a perspective view of a reservoir of the cooling system of FIG. 9.
Figure 11:
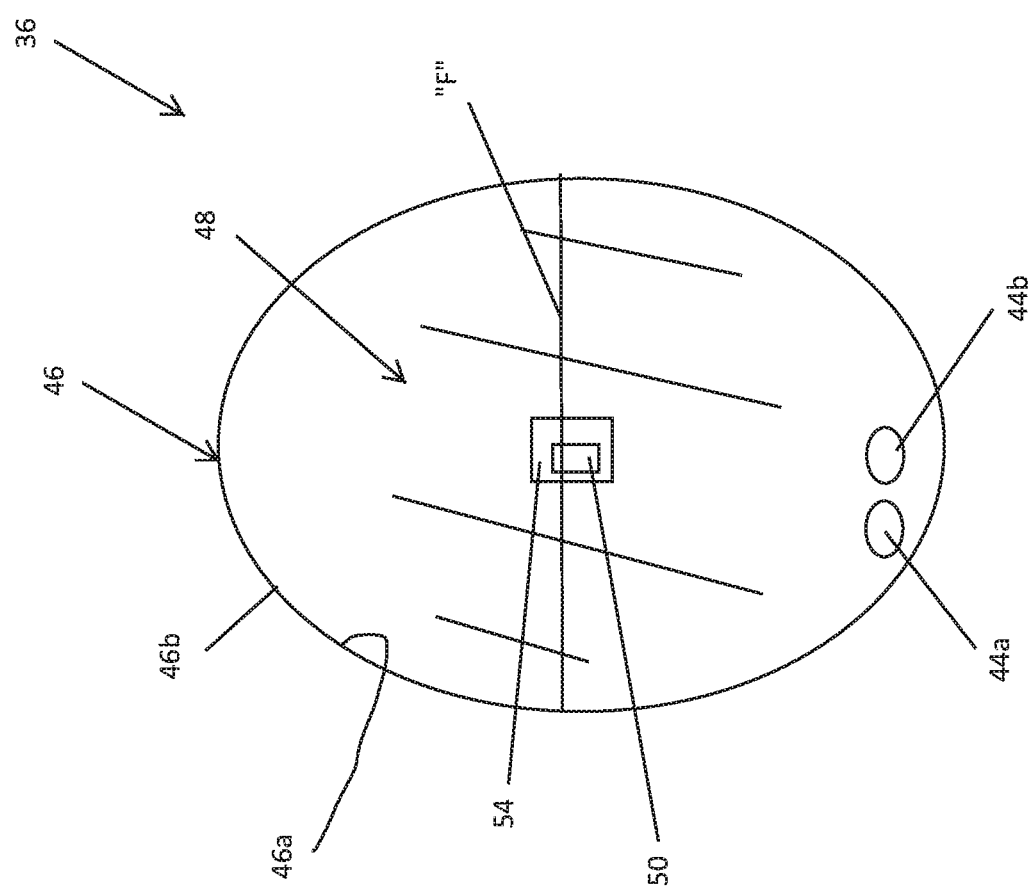
FIG. 11 is a perspective view of another embodiment of a reservoir of the coolant system of FIG. 9.

With reference to FIGS. 9-11, another embodiment of an ablation system is provided. The ablation system 10 generally includes a microwave ablation probe 12, a microwave generator 14, and a medical ablation device cooling system 34. The generator 14 is configured to provide microwave energy at an operational frequency from about 500 MHz to about 5000 MHz, although other suitable frequencies are also contemplated. In some embodiments, the generator 14 may generate any suitable type of energy, for example, RF energy, or ultrasonic energy.

The probe 12 and the generator 14 are coupled to one another via a connector assembly 16 and a cable assembly 20. The connector assembly 16 is a cable connector suitable to operably connect the cable assembly 20 to the generator 14. The connector assembly 16 may house a memory (e.g., an EEPROM) storing a variety of information regarding various components of the system 10. For example, the memory may store identification information that can be used by the generator 14 to determine the identification of probes connected to the generator 14. Based on the determined identification of a probe, the generator 14 may or may not provide energy to the probe. For example, if the identification information stored in memory does not match identification information provided by the probe (e.g., via a RFID tag on the probe), the generator 14 will not provide energy to the connected probe.

The cable assembly 20 interconnects the connector assembly 16 and the probe 12 to allow for the transfer of energy from the generator 14 to the probe 12. The cable assembly 20 may be any suitable, flexible transmission line, such as a coaxial cable, including an inner conductor, a dielectric material coaxially surrounding the inner conductor, and an outer conductor coaxially surrounding the dielectric material. The cable assembly 20 may be provided with an outer coating or sleeve disposed about the outer conductor. The sleeve may be formed of any suitable insulative material, and may be applied by any suitable method, e.g., heat shrinking, over-molding, coating, spraying, dipping, powder coating, and/or film deposition.

The probe 12 includes a radiating portion 18 that radiates energy provided by the generator 14. The radiating portion 18 is coupled to the cable assembly 20 through a handle assembly 22. The handle assembly 22 has an outlet fluid port 30 and an inlet fluid port 32 each in fluid communication with an interior chamber (not explicitly shown) defined in the probe 12. Thus, the cooling fluid may circulate from the ports 30 and 32 around the interior chamber or chambers of the probe 12 to cool the probe 12 during use. The ports 30 and 32 of the handle assembly 22 are coupled to the cooling system 34 via outlet and inlet tubes 38, 40, respectively.

For a more detailed description of a microwave ablation system, reference may be made to U.S. Patent Application Publication No. 2014/0276033, filed on Mar. 15, 2013, the entire contents of which are incorporated by reference herein.

With reference to FIG. 10, the cooling system 34, similar to the cooling system 1000 of FIGS. 1-6, includes a reservoir 36 and a supply pump (not explicitly shown). The supply pump may be a peristaltic pump, such as the peristaltic pump 600 of FIGS. 1-6, or any other suitable pump configured to circulate cooling fluid "F" (FIG. 10) from the reservoir 36 and into the probe 12. The reservoir 36 stores the cooling fluid "F" and may be in the form of a saline bag or any other suitable container for holding the cooling fluid "F" (e.g., saline, water, etc.). In embodiments, the cooling system 34 may incorporate some or all of the features of the cooling system 1000 of FIGS. 1-6, such as, for example, the reservoir connector assembly 100, the drip chamber 300, the tubing system 400, and the elbow member 500.

The reservoir 36 includes an outlet fluid port 44a, similar to the lumen 107 of FIG. 2, coupled to the outlet tube 38 (FIG. 9), and an inlet fluid port 44b, similar to the lumen 105 of FIG. 2, coupled to the inlet tube 40 (FIG. 9). The reservoir 36 has a wall 46 fabricated from a flexible material, such as, for example, polyvinyl chloride (PVC), polyolefins, nylon, or a composite thereof. The wall 46 has an inner peripheral surface 46a defining an inner chamber 48, and an outer peripheral surface 46b. The chamber 48 is in fluid communication with the outlet and inlet fluid ports 44a, 44b, such that the cooling fluid "F" may be circulated out of the chamber 48 via the outlet fluid port 44a, into the probe 12 (FIG. 9) to cool the probe 12, and returned back to the chamber 48 via the inlet fluid port 44b.

The cooling system 34 further includes a thermochromic material 50 thermally coupled to the cooling fluid "F" for providing a visual indication of a temperature of the cooling fluid "F" during use of the ablation system 10. The thermochromic material 50 may be a thermochromic paper, polymer, and/or ink and is configured to change its color in response to a change in temperature of the cooling fluid "F." For example, the thermochromic material 50 may be configured to exhibit a first color when the cooling fluid "F" is at or below a threshold temperature, and may exhibit a second color, different from the first color, when the cooling fluid "F" is above the threshold temperature.

The first color of the thermochromic material may be one that is typically used as an identifier of cooler temperatures, and the second color may be one that is typically used as an identifier of warmer temperatures. For example, the first color may be blue, black or green, and the second color may be red, orange, white, or yellow. In embodiments, any suitable color may be selected to visually indicate the change in temperature of the cooling fluid "F." The threshold temperature at which the hermochromic material 50 is configured to transition is between approximately 10° C. and approximately 60° C., and in some embodiments, may be approximately 30° C. In embodiments, the thermochromic material 50 may be configured to exhibit more than two colors, such as, for example, three or more colors with each corresponding to a discreet temperature or temperature range of the cooling fluid "F."

In one embodiment, the thermochromic material 50 may be coupled directly or indirectly to the inner or outer peripheral surfaces 46a, 46b of the wall 46. One or both of the inner and outer peripheral surfaces 46a, 46b of the wall 46 may have a laser-marked symbol having the same color as the thermochromic material 50 when the thermochromic material 50 is cool, such that the laser-marked symbol reveals itself after the thermochromic material 50 warms. In other embodiments, the laser-marked symbol may have the same color as the thermochromic material 50 when the thermochromic material 50 is warm.

The reservoir 36 may have a sticker 52 incorporating the thermochromic material 50 and may be adhered to the wall 46 of the reservoir 36. In this way, as the temperature of the cooling fluid "F" reaches the threshold temperature, the thermochromic material 50 changes from the first color to the second color to indicate to the clinician that the cooling fluid "F" is at a temperature unsuitable for cooling the probe 12, and therefore should be changed.

FIG. 11 illustrates an embodiment of the reservoir 36 that includes a float 54 disposed within the chamber 48 thereof for indicating the level of the cooling fluid "F." The float 54 may have the thermochromic material 50 coupled thereto. In this way, the float 54 serves the dual function of indicating the level of the cooling fluid "F" while also providing a visual cue of the temperature of the cooling fluid "F." It is contemplated that the float may be fabricated from a plastic thermochromic material 50.

In yet another embodiment (not explicitly shown), the thermochromic material 50 may be coupled to the drip chamber 300 of the cooling system 1000 of FIGS. 1-6. It is contemplated that the thermochromic material 50, whether incorporated into the float 54 or the sticker 52, may be coupled to the reservoir 200, the drip chamber 300, the tubing system 400, or the elbow member 500 of the cooling system 1000.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figs. are presented only to demonstrate certain examples of the disclosure. Other elements, steps, methods, and techniques that are insubstantially different from those described above and/or in the appended claims are also intended to be within the scope of the disclosure.

What is claimed is:

1. A medical ablation device cooling system, comprising:
an outlet tube configured to be coupled to an outlet fluid port of an ablation probe and an inlet tube configured to be coupled to an inlet fluid port of the ablation probe;
a reservoir containing a cooling fluid and configured to be coupled to the ablation probe via the outlet and inlet tubes;
a float disposed within the reservoir for indicating the level of the cooling fluid within the reservoir; and
a thermochromic material disposed on the float and thermally coupled to the cooling fluid of the reservoir, wherein the thermochromic material is configured to exhibit a first color when the cooling fluid is below a threshold temperature, and a second color when the cooling fluid is above the threshold temperature.

2. The medical ablation device cooling system according to claim 1, wherein the first color is associated with a cool temperature, and the second color is associated with a warm temperature.

3. The medical ablation device cooling system according to claim 2, wherein the threshold temperature is between approximately 10° C. and approximately 60° C.

4. The medical ablation device cooling system according to claim 1, further comprising:
- a drip chamber fluidly coupling the reservoir and the outlet tube; and
- another thermochromic material coupled to the drip chamber.

5. The medical ablation device cooling system according to claim 1, wherein the reservoir is a saline bag.

6. The medical ablation cooling system according to claim 1, wherein the float is fabricated from the thermochromic material.

7. A reservoir for supplying a cooling fluid to a medical ablation probe, comprising:
- a wall defining a chamber therein;
- an outlet fluid port and an inlet fluid port each in fluid communication with the chamber;
- a cooling fluid disposed within the chamber;
- a float disposed within the chamber for indicating a level of the cooling fluid disposed within the chamber; and
- a thermochromic material disposed on the float and thermally coupled to the cooling fluid, wherein the thermochromic material is configured to exhibit a first color when the cooling fluid is below a threshold temperature, and a second color when the cooling fluid is above the threshold temperature.

8. The reservoir according to claim 7, wherein the first color is associated with a cool temperature, and the second color is associated with a warm temperature.

9. The reservoir according to claim 7, wherein the threshold temperature is between approximately 10° C. and approximately 60° C.

\* \* \* \* \*